United States Patent
Mendelsohn et al.

(10) Patent No.: US 11,931,453 B2
(45) Date of Patent: **\*Mar. 19, 2024**

(54) DRUG DELIVERY DEVICE

(71) Applicant: NANO PRECISION MEDICAL, INC., Emeryville, CA (US)

(72) Inventors: Adam D. Mendelsohn, Emeryville, CA (US); Kathleen E. Fischer, Emeryville, CA (US); Tomoyuki Yoshie, Emeryville, CA (US); Wouter Roorda, Emeryville, CA (US)

(73) Assignee: Nano Precision Medical, Inc., Emeryville, CA (US)

( * ) Notice: Subject to any disclaimer, the term of this patent is extended or adjusted under 35 U.S.C. 154(b) by 323 days.

This patent is subject to a terminal disclaimer.

(21) Appl. No.: 17/468,558

(22) Filed: Sep. 7, 2021

(65) Prior Publication Data
US 2021/0401735 A1 Dec. 30, 2021

Related U.S. Application Data

(63) Continuation of application No. 16/204,890, filed on Nov. 29, 2018, now Pat. No. 11,129,791, which is a (Continued)

(51) Int. Cl.
*A61K 9/00* (2006.01)
*A61K 9/48* (2006.01)
*A61K 38/26* (2006.01)

(52) U.S. Cl.
CPC .......... *A61K 9/0024* (2013.01); *A61K 9/4808* (2013.01); *A61K 9/4816* (2013.01); *A61K 38/26* (2013.01)

(58) Field of Classification Search
CPC .. A61K 9/0024; A61K 9/4808; A61K 9/4816; A61K 38/26
See application file for complete search history.

(56) References Cited

U.S. PATENT DOCUMENTS 5,972,369 A * 10/1999 Roorda ................ A61K 31/675
424/424
7,687,431 B2 3/2010 Nakayama et al.
(Continued)

FOREIGN PATENT DOCUMENTS

| WO | 2013085951 A1 | 6/2013 |
| WO | 2015112811 A1 | 7/2015 |
| WO | 2016070117 A1 | 5/2016 |

OTHER PUBLICATIONS

U.S. Appl. No. 16/204,890, Advisory Action dated Apr. 30, 2021, 5 pages.
(Continued)

*Primary Examiner* — Lauren P Farrar
(74) *Attorney, Agent, or Firm* — Kilpatrick Townsend & Stockton LLP

(57) ABSTRACT

Embodiments of the invention include devices, compositions and methods for the controlled release of therapeutic substances, such as drugs. Control over the rate of release of the therapeutic substances from the devices is achieved by the use of nanoporous membranes in which the pore size is matched to the molecular diameter of the therapeutic substances. Some embodiments of the invention achieve zero-order release by the use of membranes with a pore diameter that is more than five times the Stokes' diameter of the therapeutic substance released.

12 Claims, 7 Drawing Sheets

Related U.S. Application Data continuation of application No. PCT/US2017/036845, filed on Jun. 9, 2017.

(60) Provisional application No. 62/349,595, filed on Jun. 13, 2016.

(56) References Cited

U.S. PATENT DOCUMENTS

| | | | |
|---|---|---|---|
| 7,955,614 B2 * | 6/2011 | Martin | A61K 38/38 |
| | | | 424/423 |
| 9,511,212 B2 | 12/2016 | Roorda | |
| 10,479,868 B2 | 11/2019 | Mendelsohn et al. | |
| 10,525,248 B2 | 1/2020 | Roorda et al. | |
| 2009/0061071 A1 * | 3/2009 | McMorrow | A61L 31/14 |
| | | | 427/2.14 |
| 2013/0172250 A1 | 7/2013 | Fineman et al. | |
| 2014/0371687 A1 * | 12/2014 | Mendelsohn | B82Y 30/00 |
| | | | 604/286 |
| 2019/0091140 A1 | 3/2019 | Mendelsohn et al. | |
| 2019/0217070 A1 | 7/2019 | Eversull et al. | |
| 2020/0040140 A1 | 2/2020 | Mendelsohn et al. | |

OTHER PUBLICATIONS

U.S. Appl. No. 16/204,890, Final Office Action dated Dec. 9, 2020, 12 pages.
U.S. Appl. No. 16/204,890, Non-Final Office Action dated May 14, 2020, 8 pages.
U.S. Appl. No. 16/204,890, Notice of Allowance dated Jun. 2, 2021, 7 pages.
International Application No. PCT/US2017/036845, International Search Report and Written Opinion dated Aug. 30, 2017, 13 pages.

* cited by examiner

DRUG DELIVERY DEVICE

CROSS-REFERENCE TO RELATED APPLICATIONS

The present application is a continuation of U.S. patent application Ser. No. 16/204,890, filed Nov. 29, 2018, allowed, which application is a continuation of PCT Application No. PCT/US2017/036845, filed Jun. 9, 2017, which claims priority to U.S. Provisional Patent Application No. 62/349,595, filed Jun. 13, 2016, the disclosures of which are hereby incorporated by reference in their entirety for all purposes.

BACKGROUND OF THE INVENTION

Many beneficial substances require long-term delivery to a subject to be optimally effective. Well-known examples include therapeutic agents that need to be administered for extended periods of time to a patient. Many extended release compositions have been developed for this purpose. A common issue with all of these compositions is that the agents administered need to be stabilized in the composition for the duration of shelf-life of the dosage form, in addition to the stabilization required during the extended release period. Typically, solid state compositions offer superior stability over liquid compositions. In addition, a zero-order release rate of therapeutic agents is often a desired feature.

Many devices having a release rate controlling membrane and a reservoir containing a solid state composition of a therapeutic agent have been described. Often, such compositions have to be hydrated to bring the therapeutic agents in solution in order to enable diffusion and their release. Peptides and proteins form an increasingly important group of therapeutic agents. Generally, slow hydration of peptides and proteins tends to cause stability problems, like irreversible aggregation. Similar aggregation has been observed when peptides and proteins are formulated at sufficiently high concentrations to provide long term release of these compounds. In addition, peptides and proteins do not diffuse adequately through most release rate controlling membranes.

Therefore, there is need for a novel controlled release membrane technology that allows for sustained release of peptides and proteins from devices containing a sufficiently high concentration of these therapeutics, either in a solid state or in a concentrated solution, to provide a meaningful duration of therapy. The present invention satisfies these and other needs.

BRIEF SUMMARY OF THE INVENTION

The present invention generally relates to devices and methods for zero order delivery of therapeutic agents. Exemplary embodiments of the invention are described in this summary.

In one embodiment, the present invention provides an implantable device for zero-order release of a therapeutic agent, the device comprising:
  a capsule suitable for implantation;
  a reservoir encapsulated by the capsule, the reservoir suitable for containing a pharmaceutically acceptable formulation of the therapeutic agent; and
  at least one nanoporous membrane in fluid contact with the reservoir, wherein the nanoporous membrane comprises nanopores having diameters more than 5 times greater than the molecular diameter of the therapeutic agent.

In certain instances, the diameters of the nanopores can be monodisperse or polydisperse.

The implantable device as described herein, wherein the average diameter of the pores is between 6.4 and 7.5 times a molecular diameter of the therapeutic agent.

The implantable device as described herein, wherein the molecular diameter is the Stokes' diameter of molecules of the therapeutic agent.

The implantable device as described herein, wherein the nanoporous membrane is a titania nanotube membrane. In certain instances, the titania nanotubes can be attached to a titanium substrate.

The implantable device as described herein, wherein the pharmaceutically acceptable formulation comprises a solid state form of the therapeutic agent.

The implantable device as described herein, wherein the pharmaceutically acceptable formulation comprises the solid state form of the therapeutic agent suspended in a liquid carrier.

The implantable device as described herein, wherein the therapeutic agent is one of a peptide and a protein.

The implantable device as described herein, wherein the therapeutic agent is a GLP-1 agonist.

The implantable device as described herein, wherein the therapeutic agent is exenatide.

The implantable device as described herein, wherein exenatide is present in an amount between about 60 micrograms and about 50 milligrams.

In another embodiment, the present invention provides a method for treating a disease in a subject in need thereof, the method comprising:
  administering to the subject an implantable device for zero-order release of a therapeutic agent, the device comprising:
  a capsule suitable for implantation;
  a reservoir encapsulated by the capsule, the reservoir suitable for containing a pharmaceutically acceptable formulation of the therapeutic agent; and
  at least one nanoporous membrane in fluid contact with the reservoir, wherein the nanoporous membrane comprises nanopore having diameters more than 5 times greater than the molecular diameter of the therapeutic agent.

In certain instances, the diameters of the nanopores can be monodisperse or polydisperse.

The method as described herein, wherein the device is implanted subcutaneously.

The method as described herein, wherein the device is implanted non-surgically by means of a hollow implantation needle.

The method as described herein, wherein the average diameter of the pores is between 6.4 and 7.5 times a molecular diameter of the therapeutic agent.

The method as described herein, wherein the molecular diameter is a Stokes' diameter of molecules of the therapeutic agent.

The method as described herein, wherein the nanoporous membrane is a titania nanotube membrane. In certain instances, the titania nanotubes can be attached to a titanium substrate.

The method as described herein, wherein the pharmaceutically acceptable formulation comprises a solid state form of the therapeutic agent.

The method as described herein, wherein the pharmaceutically acceptable formulation comprises the solid state form of the therapeutic agent suspended in a liquid carrier.

The method as described herein, wherein the therapeutic agent is one of a peptide and a protein.

The method as described herein, wherein the therapeutic agent is a GLP-1 agonist.

The method as described herein, wherein the therapeutic agent is exenatide.

The method as described herein, wherein exenatide is present in an amount between about 60 micrograms and about 50 milligrams.

The method as described herein, wherein the disease is type 2 diabetes.

The method as described herein, wherein the mean steady-state plasma concentration of exenatide is 170 pg/ml to 600 pg/ml.

The method as described herein 24, wherein the mean steady state plasma concentration of exenatide is 170 pg/ml to 350 pg/ml.

The method as described herein, wherein the mean steady state plasma concentration of exenatide is 170 pg/ml to 290 pg/ml.

The method as described herein, wherein the therapeutic agent provides therapy from 30 days to about 1 year.

These and other aspects, objects and embodiments will become more apparent when read with the detailed description and figures that follow.

DETAILED DESCRIPTION OF THE INVENTION

Definitions

"Fickian diffusion" includes diffusion that is dependent on a concentration gradient in accordance with Fick's Laws of diffusion.

"Fluid contact" includes a location of two or more entities relative to each other in a manner that allows for fluid-phase mass transport between the entities.

"Membrane" includes a porous structure allowing mass transport of molecules from one side of the structure to the other through the structure.

"Nanoporous membrane" includes a porous structure wherein at least some of its pores are open on both ends and form fluid-filled pathways having a smallest dimension less than one micrometer and allowing for mass transport through the structure.

"Peptide," and "protein" are used herein to include oligomers and polymers of amino acid residues. Both terms apply to amino acid chains in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full length proteins, wherein the amino acid residues are linked by covalent peptide bonds. A definition used by the United States Food and Drug Administration defines peptides as amino acid chains of 40 amino acids or less.

The phrase "a monodispersity of nanopore diameters" includes a homogeneous distribution or uniform collection of sizes of diameters of nanopores, in other words: a nanoporous membrane having pores sizes with a tight distribution of diameters. For the purpose of this disclosure, in a monodisperse distribution at least 95% of the pores have a diameter within a range no greater than an average +/−10%.

The phrase "a polydispersity of nanopore diameters" includes a heterogeneous distribution or non-uniform collection of sizes of diameters of nanopores, in other words nanoporous membrane having pores sizes with a wide distribution of diameters. For the purpose of this disclosure, any pore size distribution with a range larger than a monodisperse distribution is a polydisperse distribution i.e., greater than an average +/−10%.

Figure 7:
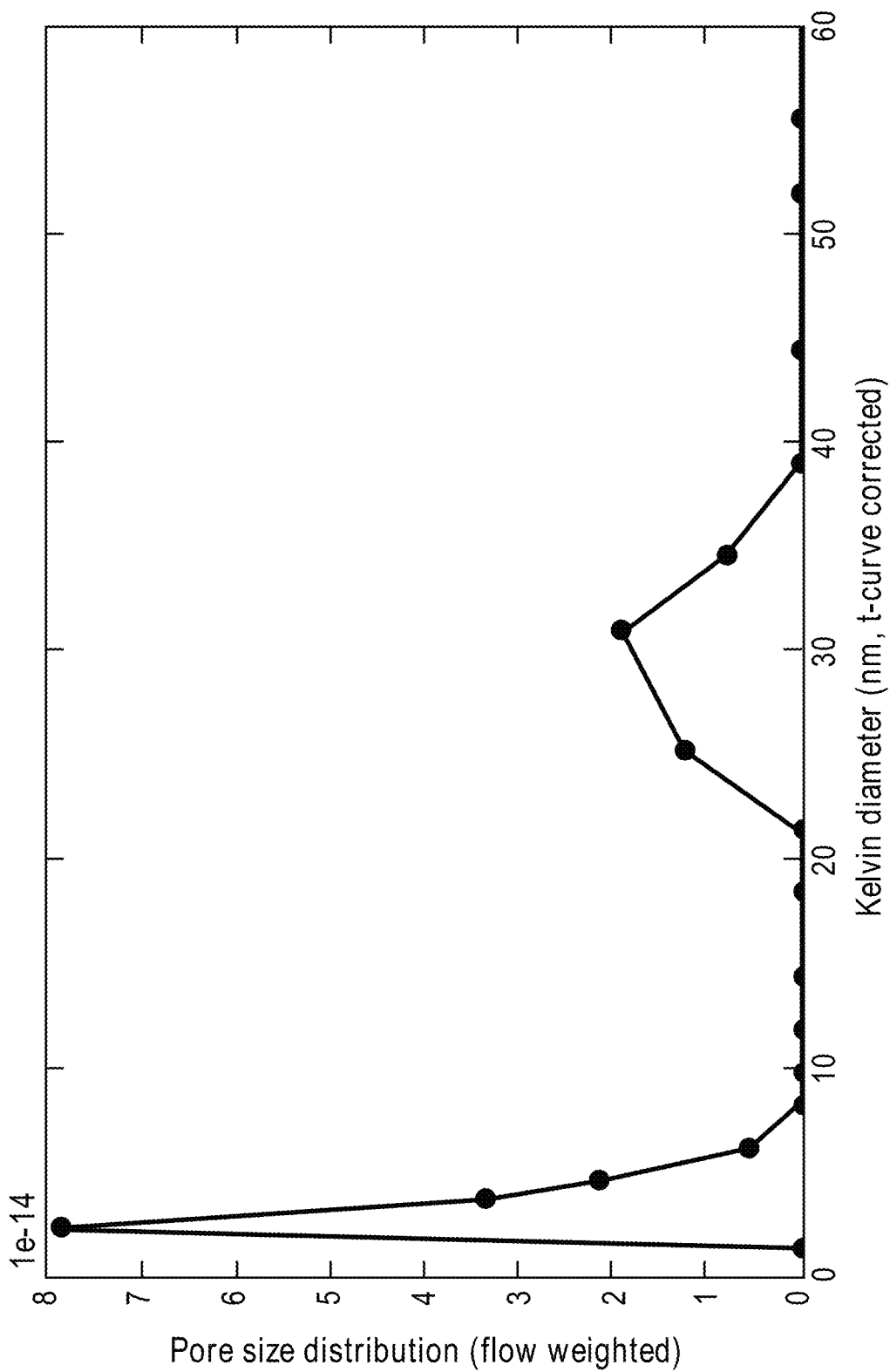
FIG. 7 illustrates one embodiment having a bimodal distribution (e.g., polydispersity) of pore sizes.

The "modality" of a pore size distribution refers to the number of maxima observed in a representation of a pore size distribution, such as a histogram. Uni-modal distribution refers to a distribution with 1 maximum, bi-modal to a distribution with 2 maxima, etc. Poly-modal may generally refer to distributions with more than 1 maximum. An example of a bi-modal distribution is shown in FIG. 7. A uni-modal distribution, with a distribution of at least 95% of the pores within a range no greater than an average +/−10% qualifies as a mono-disperse distribution. A unimodal distribution can be monodisperse or polydisperse. In certain instances, polymodal distributions will be polydisperse.

The term "polymer" includes any molecule composed of more than three monomeric subunits.

"Stokes' diameter" or "hydrodynamic diameter" includes the dimension of a molecule plus its associated water molecules as it moves through an aqueous solution, and is defined as the diameter of an equivalent hard sphere diffusing at the same rate as the molecule under observation.

"Subject" includes animals such as mammals, including, but not limited to, primates (e.g., humans), cows, sheep, goats, horses, dogs, cats, rabbits, rats, mice and the like. In certain embodiments, the subject is a human.

"Therapeutic agent" includes any agent capable of providing a therapeutic response, such as a drug or biologic.

"Titanium" is element number 22.

"Titania" is titanium dioxide ($TiO_2$).

"Titania nanotube membrane" includes a nanoporous membrane having an array of titania nanotubes on a titanium substrate where at least a portion of the titania nanotubes are open at both ends and capable of allowing mass transport from one side of the membrane to the other through the titania nanotubes.

"Therapeutically effective amount or dose" or "therapeutically sufficient amount or dose" or "effective or sufficient amount or dose" includes a dose that produces therapeutic effects for which it is administered. The exact dose will depend on the purpose of the treatment, and will be ascertainable by one skilled in the art using known techniques (see, e.g., Lieberman, Pharmaceutical Dosage Forms (vols. 1 3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). In sensitized cells, the therapeutically effective dose can often be lower than the conventional therapeutically effective dose for non-sensitized cells.

"Zero-order release" includes a release rate profile that is independent of a concentration gradient and that approaches a constant or near-constant release rate.

The invention pertains to devices, methods and compositions for an extended release of a beneficial substance such as therapeutic agents, and to methods of treating patients in need of treatment with the therapeutic agents. In some embodiments, of the invention, the devices are implantable devices.

Figure 1:
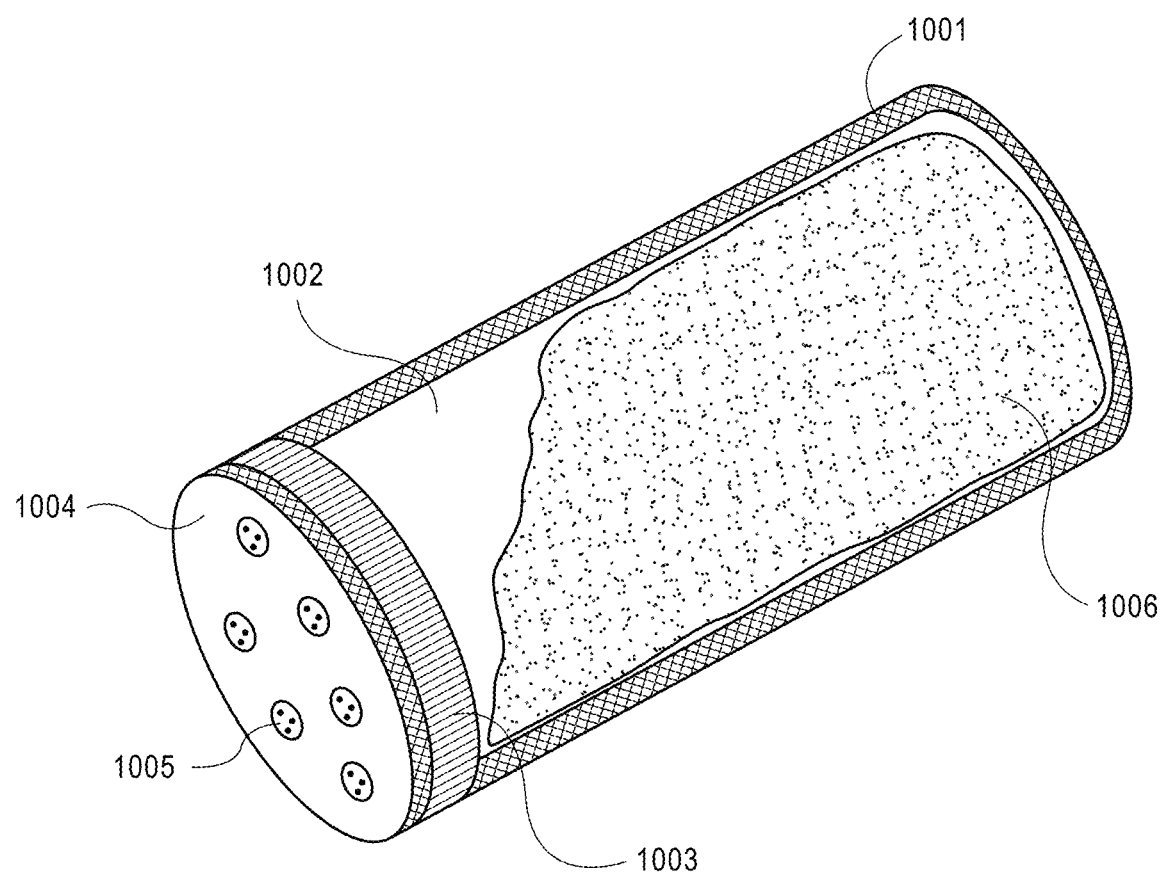
FIG. 1 illustrates a schematic drawing of a representative embodiment of the invention.

A representative embodiment of the invention is illustrated in FIG. 1. As shown therein, capsule 1001 encapsulates reservoir 1002. A nanoporous membrane 1003 is located at one end of capsule 1001. The nanoporous membrane is supported by a titanium substrate 1004. Titanium substrate 1004 has a number of windows 1005. Titanium substrate 1004 provides a physical support for membrane 1003, while windows 1005 provide apertures for mass transport. A composition 1006 of a therapeutic agent is contained within reservoir 1002. In one embodiment of FIG. 1, the composition is a solid state composition.

During hydration, liquid enters reservoir 1002 through nanoporous membrane 1003, and starts to dissolve composition 1006. A liquid composition of the therapeutic agent is formed inside reservoir 1002, enabling diffusion of the therapeutic agent through nanoporous 1003 membrane and out of the reservoir 1002.

While a rod-shaped capsule like the one illustrated in FIG. 1 may be desirable for ease of implantation, for instance by means of a trocar system or hollow needle, the invention is not limited to a particular shape of capsule, and any suitable type of shape may be employed. Likewise, the membrane may be located on any suitable location of the capsule, and more than one membrane may be present. A membrane may be oriented with the nanotubes facing inward into the reservoir of the device, or facing outward towards the environment of the device.

Composition 1006 may be any type of suitable composition, including solid and liquid compositions, as well as mixed compositions like a suspension of solids in a liquid.

In some embodiments, devices of the invention have a reservoir containing a pharmaceutically acceptable composition of a therapeutic agent, and at least one membrane configured to achieve the extended release by controlling the rate of release of the therapeutic agent from the reservoir. In some embodiments, the extended release is a zero-order release. In some embodiments, the compositions are solid-state compositions. In some embodiments, the therapeutic agents are peptides or proteins. In some embodiments, the reservoir has a volume between 5 microliters and 5 milliliters. In preferred embodiments the reservoir has a volume between 10 microliters and 500 microliters.

In certain instances, the device has a reservoir capacity with a volume of about 10 microliters to about 10 milliliters. In certain instances, the reservoir has a volume of about 10 µl to about 100 µl such as 10, 20, 25, 30, 35, 40, 45, 50, 55, 60, 70, 80, 90, or 100 µl. In other instances, the reservoir is about 25-60 µl or about 30-50 or even about 30-45 µl. In other instances, the reservoir is about 100-500 microliters, 150-450 microliters, or about 150-350 microliters, such as about 250 microliters.

In some embodiments, the membrane controlling the rate of release of the therapeutic agent is a nanoporous membrane. In some embodiments, the nanoporous membrane is a titania nanotube membrane. In certain instances, the titania nanotubes can be attached to a titanium substrate. In certain embodiments, there are two or more membranes in the device. In some embodiments, compositions of the invention are disposed within a reservoir of an extended release dosage form, such as a capsule encapsulating the reservoir, controlled by a nanoporous membrane, wherein the nanoporous membrane is configured to achieve extended release of the therapeutic agent from the reservoir of a device. In some embodiments, the nanoporous membrane is configured to achieve extended release through a non-Fickian diffusion mechanism. In some embodiments, the nanoporous membrane is configured to achieve extended release through a non-Fickian diffusion mechanism that produces zero-order release rates.

In some embodiments, the release rate of the therapeutic agent is controlled by matching the dimensions of pores in the nanoporous membrane to molecular dimensions of the therapeutic agent. In some embodiments, pores in the nanoporous membrane are matched to the molecular diameter (e.g. the Stokes' diameter) of the molecules of the therapeutic agent. In some embodiments, the pores in the nanoporous membrane have a diameter that is more than five times the molecular diameter of the therapeutic agent.

In certain instances, the pores of the nanoporous membrane have a uniform distribution of diameters or in other words the pores are monodisperse. The diameters of the nanopores may be within a range between 1 nm to about 100 nm. The diameters of the pores may have a single Gaussian or bell-shape curve (or other shapes) of various diameters. A distribution with a single Gaussian or bell-shape curve (or other shapes) may be termed a unimodal distribution. In a monodisperse distribution at least 95% of the pores have a diameter within a range no greater than an average +/−10%.

In certain instances, the pores of the nanoporous membrane have a non-uniform distribution of diameters. The diameters of the pores may be within a range between 1 nm to about 100 nm. The diameters of the pores may have a single distribution of diameters such as a single Gaussian or bell-shape curve (or other shapes) of various diameters, but wider than for a monodisperse distribution. In certain instances, the diameters of the pores may have more than 1 Gaussian distribution of diameters such as two or more Gaussian or bell-shape curves (or other shapes) of various diameters. Alternatively, the diameters may be bi-modal, or tri-modal distributions with 2 or 3 Gaussian or bell-shape curves (or other shapes) of distributions, or generally polymodal distributions (plural modalities). The 1, 2, 3 or more bell curves of distributions may be between 1-100 nm, 1-50 nm or 1-40 nm. For example, there can be 2 distributions. The first distribution can be between about 2-8 nm and the second distribution can be between 20-40 nm (bi-modal). In view of the foregoing, there can be 1, 2, 3, 4, 5, or more distributions each having various shapes and various ranges between 1-100 nm, or 1-50 nm, such as 5, 10, 15, 20, 25, 30, 35, 40, 45, or 50 nm.

In certain instances, the percent of nanopores between 1 nm and 50 nm can vary. For example, there can be 1% to 100% of the nanopores such as 10, 20, 30, 40, 50, 60, 70, 80 or 90% of the nanopores having a diameter of about 20 nm to about 40 nm. In another aspect, there can be 1% to about 60% of the nanopores such as 10, 20, 30, 40, or 50% of the nanopores having a diameter of about 2 nm to about 12 nm. In other aspects, there can be 1% to about 60% of the nanopores such as 10, 20, 30, 40, or 50% of the nanopores having a diameter of about 15 nm to about 20 nm.

In certain instances, at least 90, 91, 92, 93, 94, 95, 96, 97, 98, or 99 percent of the cross-sectional surface area ($nm^2$) is provided by nanopores with a diameter greater than 5 times to about 19 times such as 6, 7, 8, 9, 10, 11, 12, 13, 14, 15, 16, 17, or 18 times, the molecular diameter of the therapeutic agent. In certain instances, 97 percent of the cross-sectional surface area is provided by nanopores with a diameter, which is greater than 5 times to about 19 times the molecular diameter of the therapeutic agent.

In some embodiments, the pores in the membranes are nanochannels, such as those disclosed in U.S. Pat. No. 8,480,637 incorporated herein by reference. In some embodiments, the pores in the membranes are nanotubes. In some embodiments, the nanotubes are titania nanotubes, such as those disclosed in U.S. Patent Application Pub. No. 2014/0371687 incorporated herein by reference. Some embodiments of the invention comprise devices with membranes mounted with nanotubes facing towards the interior reservoir of the devices. Some embodiments of the invention comprise devices with nanotubes facing towards the external environment of the devices.

Achieving a zero-order release of a therapeutic agent from a pharmaceutical dosage form is often desired in order to achieve a sustained plasma concentration—time profile within a target range in a subject, such as a patient being treated with the therapeutic substance. Typically, the release of a therapeutic agent from a dosage form is achieved by diffusion, wherein the diffusion is controlled by mechanisms according to Fick's Laws of diffusion. In a simplified form of Fick's first law of diffusion, it may be described as follows:

$$F = D \times A \times \Delta C / l$$

wherein:
F=Rate of diffusion or Flux
D=Diffusion coefficient of the diffusing species
A=Cross-sectional area of diffusion, and
$\Delta C/l$=Concentration gradient Therefore, in typical Fickian diffusion, the rate of diffusion is proportional to the concentration gradient. In many cases of controlled drug delivery this principle has been employed by creating membrane controlled dosage forms having a reservoir and a rate controlling membrane, wherein the reservoir contains a saturated solution of a therapeutic agent plus excess solid therapeutic agent. As long as excess solid therapeutic agent is present, the solution of the therapeutic agent in the reservoir will remain saturated, thus maintaining a constant concentration gradient over the membrane, and, consequently, a constant rate of diffusion of the therapeutic agent through the membrane.

More recently, a different mechanism to achieve zero-order rates of diffusion has been described, referred to as restricted diffusion or sometimes as Knudsen diffusion. Without being bound by theory, it is believed that restricted diffusion may occur in confined channels, where interactions of the diffusion molecules with the walls of the channels are more frequent than interactions between the diffusing molecules themselves, thus imposing an alternative mechanism controlling the rate of diffusion, independent of a concentration gradient.

Zero-order release through nanoporous membranes using restricted diffusion has been disclosed in U.S. Pat. No. 8,603,076. In restricted diffusion, the inner diameter of the nanopores is tailored to the molecular dimensions of the diffusing substance, such that the diffusional mobility of the diffusing substance is restricted to produce a release rate that is independent of the concentration gradient of the diffusing substance. Previous disclosures of an inner diameter of the nanopores of 1-5 times the molecular diameter, (e.g. the Stokes' diameter) of a diffusing substance is needed to produce such zero-order release.

U.S. Pat. No. 8,603,076 discloses that pore sizes larger than 5 times a molecular diameter of a diffusing species provide release rate profiles that follow more traditional profiles, such as those controlled by Fickian diffusion.

It has now been discovered that under certain conditions, non-Fickian release, including zero-order release rate profiles, are obtained from devices having nanoporous membranes with pore size significantly larger than 5 times a molecular diameter of a diffusing species.

Embodiments of the current invention include devices and methods for producing non-Fickian release of a beneficial substance, including zero-order release rate profiles, using nanopores with an inner diameter larger than 5 times a molecular diameter of the beneficial substance. Embodiments of the invention do not rely on maintaining a saturated solution of a beneficial substance in a reservoir. Some embodiments include devices and methods to produce zero-order release of peptides and proteins.

In some embodiments, the protein or peptide therapeutic agents are Glucagon-Like Peptide-1 receptor agonists also known as GLP-1 receptor agonists. In some embodiments, the GLP-1 receptor agonist is exenatide. In certain instances, exenatide has CAS No. 141732-76-5 and an empirical formula of $C_{184}H_{282}N_{50}O_{60}S$.

Drug delivery devices containing high concentrations of exenatide, a GLP-1 agonist used to treat Type II diabetes, were found to provide extended release of exenatide according to a non-Fickian mechanism at zero-order release rate when the drug was released through a titania nanotube membrane with nanotubes having a diameter more than 5 times the estimated Stokes' diameter or hydrodynamic diameter of exenatide.

In some embodiments, the therapeutic agent is a protein or peptide.

In some embodiments, suitable peptides include, but are not limited to, beta-glucocerobrosidase, interferon alpha, interferon beta, interferon gamma, agasidase alpha, agasidase beta, exenatide, octreotide, LHRH, LHRH analogs, calcitonin, nutropin/somatropin, factor VIII, aldesleukin, forigerimod, NP fusion proteins, IL-12, a melanocyte stimulating hormone, and bapineuzumab.

In some embodiments, the protein or peptide therapeutic agents are Glucagon-Like Peptide-1 receptor agonists also known as GLP-1 receptor agonists. In some embodiments, the GLP-1 receptor agonist is exenatide. In preferred embodiments, the amount of exenatide can be from about 50 µg to about 50 mg, such as 50 µg 100 µg, 200 µg, 300 µg, 400 µg, 500 µg, 600 µg, 700 µg, 800 µg, 900 µg, 1 mg, 10 mg, 20 mg, 30 mg, 40 mg, or 50 mg.

Exenatide is an analog of GLP-1. Literature references estimate the hydrodynamic diameter of GLP-1 to be about 2.6 nm, based on the molecular dimensions of similar peptides. (Raman and Fluorescence Microscopy Studies of Lipid Membrane Structure and Drug-membrane Interactions. Christopher Bradley Fox, Proquest, 2007. Page 1530. Insulin Particle Formation in Supersaturated Aqueous Solutions of Poly(Ethylene Glycol), Lev Bromberg, Julia Rashba-Step, and Terrence Scott, Biophys J. 2005 Nov; 89(5): 3424-3433.). As further described below, zero-order release of exenatide has been observed with membranes having a nanotube diameter of more than 13 nm, such as 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48 49

The composition inside the reservoir of embodiments of the invention may be any suitable type of composition, including solid and liquid compositions, as well as mixed compositions, such as a suspension of a solid composition is a liquid carrier.

In some preferred embodiments, release of the beneficial substance(s) is extended over at least one month. In more preferred embodiments, the release is extended over at least three months, 4, 5, 6, 7, 8, 9, 10, 11, or at least 12 months.

For purposes of shelf-life and storage stability, embodiments with a solid composition are often preferred. In preferred embodiments, the compositions are non-aqueous compositions, such as a dry powder compositions or suspensions of dry powders in a non-solvent liquid. Upon hydration, for instance, during or after implantation of the device comprising the composition at a desired location in the body of a subject, components of the composition dissolve after uptake of liquid, such as physiological saline or interstitial fluid, and become available for diffusion through the nanoporous membrane.

In certain instances, it has now been found that slow hydration of certain solid-state peptide or protein compositions by uptake of aqueous liquids through a nanoporous membrane into a drug delivery device of limited size can be performed without jeopardizing the stability of the peptide or protein, and without irreversible aggregation of the peptide or protein.

Some embodiments of the invention are provided with a solid state composition of a therapeutic peptide or protein, and form liquid peptide or protein compositions with peptide or protein contents above 10% (w/w) upon hydration. Preferred embodiments of the invention form peptide or protein compositions with protein contents of at least 20% (w/w) upon hydration.

The existence of such reversible clusters would be consistent with the observed zero-order release rates of the present invention.

Compositions of the invention may be hydrated at any desired time, including at any desired time prior to implantation, for instance by submersion in a physiological saline solution, and after implantation, for instance by penetration of interstitial fluid into the reservoir. Methods to promote hydration of compositions are described in PCT/US2016/014750 and PCT/US2015/063940, both of which are incorporated herein by reference.

Additionally, it has been found that exenatide, once hydrated and in solution at high concentration, e.g. above 10% w/w in aqueous buffer systems, remains relatively stable and does not appear to form irreversible aggregates. Embodiments of the invention therefore further include devices with liquid formulations with exenatide in excess of 10% w/w.

In some embodiments, compositions of the invention comprise a beneficial substance, such as a therapeutic agent and, additionally one or more stability enhancing agents for the beneficial substance, wherein the stability enhancing agents provide further long term stability through an extended-release mechanism of the stability enhancing agent (e.g., in the form of a substance with limited solubility or a biodegradable polymer), such as disclosed in PCT/US15/58449, incorporated herein by reference.

In some embodiments, more than one beneficial substance such as a therapeutic agent is contained within the reservoir. In some embodiments, more than one stability enhancing agent is contained within the reservoir.

Embodiments of the invention therefore combine the unexpected findings that certain protein compositions can be slowly hydrated at 37° C. and form concentrated solutions without undergoing irreversible aggregation, and that such compositions are capable of producing non-Fickian release, including zero-order release rate profiles through nanoporous membranes with a pore size of more than 5 times the Stokes' diameter of the protein molecule.

Without being bound by any theory, a hypothesis has been advanced that explains both the stability of exenatide in concentrated solution as well as its zero-order release though nanopores of more than 5 times its molecular diameter, such as the Stokes' diameter, of the molecule.

If exenatide at the concentrations used in these experiments cluster into reversible, supra-molecular aggregates, then the nanotubes used in the membranes described in this disclosure might have a diameters of 1-5 times the diameter of those aggregates or supra-molecular aggregates.

Furthermore, the existence of such reversible aggregates or supra-molecular aggregates might protect the peptide from potentially damaging interactions that could lead to degradation or irreversible aggregation. Exenatide has a reported iso-electric point of 5.4 and clustering of proteins is most likely to occur at the iso-electric point, because of the lack of a net charge. Therefore, it is possible that such clusters maintain a micro-environment of a pH in that range. Generally, protein stability is enhanced at pH levels below 6, since this reduces the rate of common degradation reactions such as deamination.

Aggregation of peptides of this size is known to occur, but on a much more limited level. For example, insulin is known to form well-defined hexamer clusters. In contrast, in order to account for the observed zero-order release in the current invention, the exenatide clusters would have to be much larger than hexamers. A pore size of 50 nm would correlate with a cluster diameter of at least 10 nm, or 4 times the diameter of a single exenatide molecule. Since packing of a molecule into a three-dimensional aggregate scales with the third power of the diameter, $4^3$, or 64 exenatide molecules would have to be packed into such an aggregate.

In some embodiments, the present invention provide an implantable drug delivery device comprising a gas as a humectant, wherein the volume ratio of therapeutic agent to humectant is between 1 part of therapeutic agent to 99 parts of humectant to 99 parts of therapeutic agent and 1 part of humectant (1:99 to 99:1). The term "humectant" refers to a substance that attracts water and may function to promote hydration and, in some cases, dissolution of a composition, such as a composition of a therapeutic agent. A humectant can be a solid, a liquid or a gas as well as combinations and mixtures of the foregoing. A humicant can be a water-soluble gas.

Embodiments of the invention include methods for treating subjects having type 2 diabetes with devices of the invention releasing exenatide. The effectiveness of such treatments can be measured by determining plasma levels of exenatide upon treatment, or by determining plasma levels of hemoglobin A1C (HbA1C) upon treatment.

The doses of exenatide suitable for the treatment of type 2 diabetes can provide any suitable mean steady-state plasma concentration of the therapeutic agent in the subject. For example, the mean steady state plasma concentration can be from 10 pg/ml to 10,000 ng/ml. In some embodiments, the mean steady state plasma concentration for exenatide can be from 170 pg/ml to 600 pg/ml. In some embodiments, the mean steady state plasma concentration for exenatide can be from 170 pg/ml to 350 pg/ml. In some embodiments, the mean steady state plasma concentration for exenatide can be from 170 pg/ml to 290 pg/ml.

The doses of exenatide suitable for the treatment of type 2 diabetes can provide any suitable steady state plasma concentration of HbA1C. For example, the steady state plasma concentration of HbA1C can be lower than 10%, 9%, 8%, 7% or 6%. For example, the steady state plasma concentration of HbA1C can be lowered from baseline by at least 0.5%, at least 1%, at least 1.5% or at least 2%.

Some embodiments of the invention comprise devices as described in United States Patent Application Publication No. 2014/0371687.

Example 1

The solubility of exenatide in phosphate buffered saline was investigated by preparing solutions of increasing concentration. No clear maximum solubility could be established. A solution of 35% exenatide (w/v) is prepared with vigorous mixing and slight warming of the solution. At no time were exenatide precipitates observed.

Example 2

The stability of exenatide at high concentration inside a reservoir of a drug delivery device was investigated.

Fourteen titanium capsules (5B1-5B14) with a reservoir of 28 microliter were filled with 7 micrograms of exenatide. A titania nanotube membrane was mounted on top of the reservoir by means of a screw cap construction. The membrane comprised 5 windows, with an estimated total of about $60 \times 10^6$ nanotubes per window.

To accelerate hydration of the formulation, a vacuum was applied to the reservoirs through the nanotubes, and the evacuated reservoirs were exposed to phosphate buffered saline at room temperature for 14 days.

Figure 2:
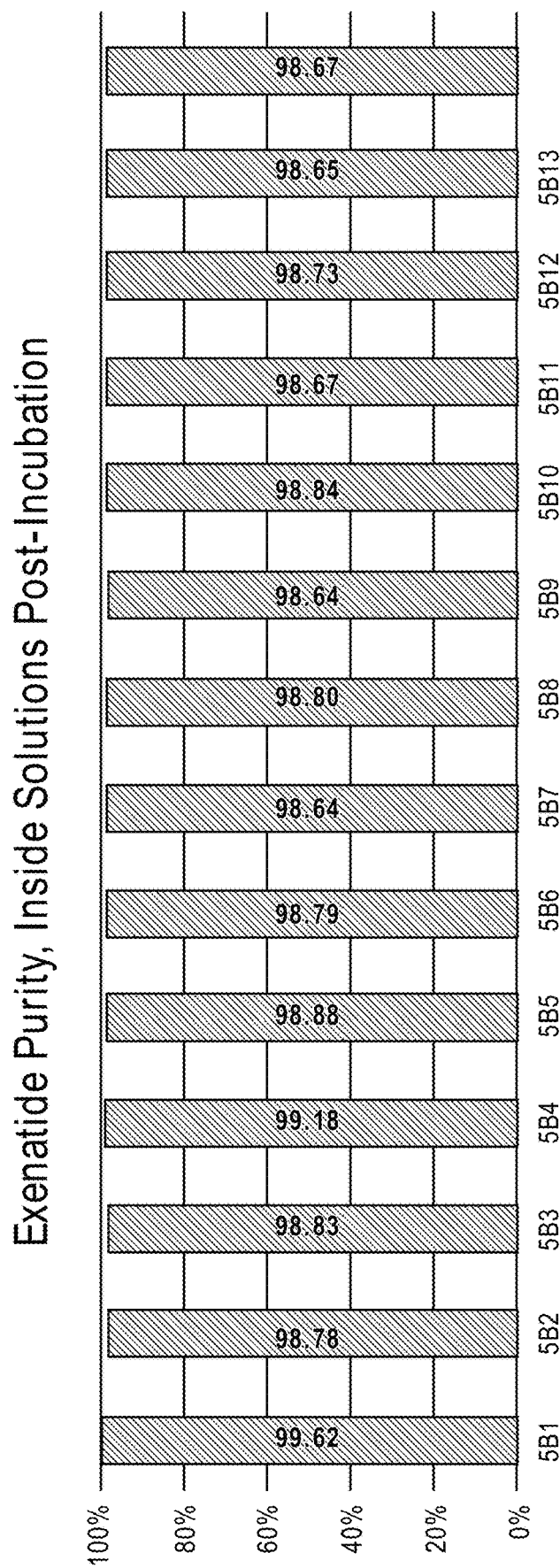
FIG. 2 illustrates the stability of exenatide after incubation for 14 days at high concentration, as measured by HPLC.

At the end of the incubation period the devices were uncapped and the internal exenatide solutions removed. No signs of solid exenatide were observed. The purity of the exenatide in solution was measured by HPLC and is plotted in FIG. 2. In all cases a purity of at least 98.6% was maintained.

Example 3

Figure 3:
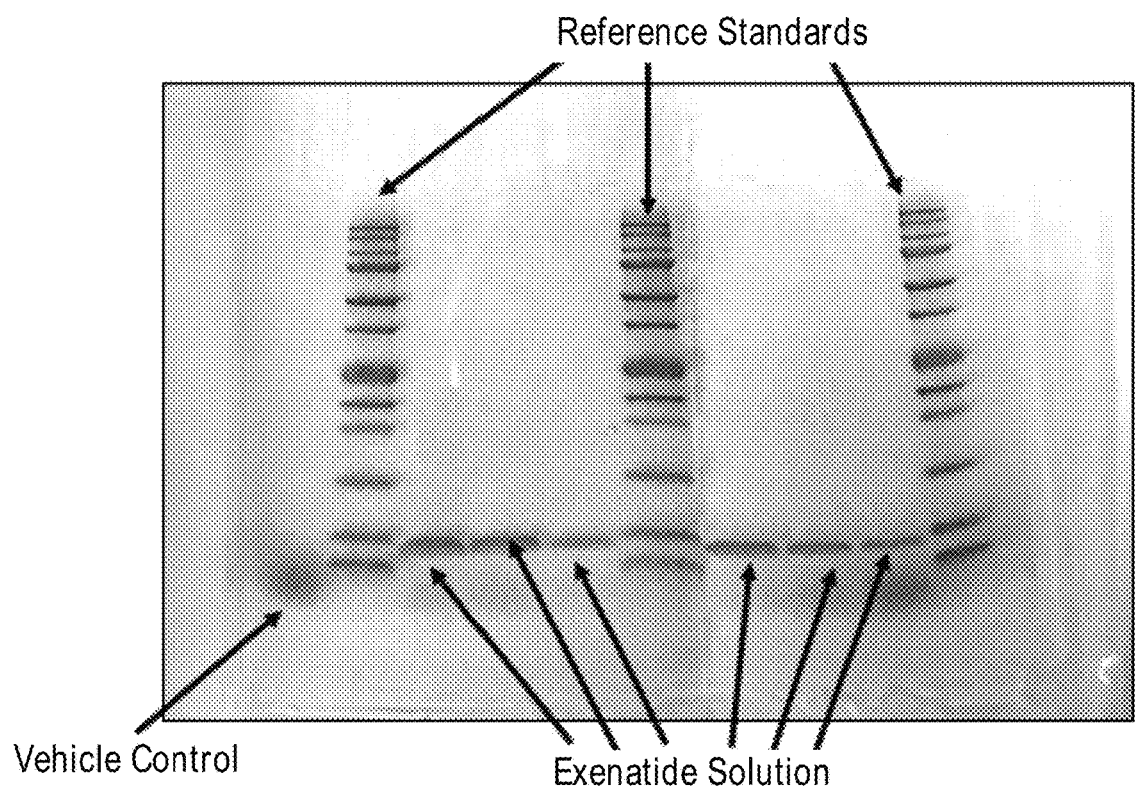
FIG. 3 illustrates the absence of higher molecular weight forms of exenatide after incubation, as measured by SDS-PAGE.

To check for the formation of irreversible aggregates of exenatide after incubation at high concentration a test was performed with SDS-PAGE electrophoresis. Sample preparation was performed analogously to Example 2. The results are shown in FIG. 3. The exenatide bands, indicated by arrows, do not show any sign of higher molecular weight exenatide aggregates. This means that, even if exenatide indeed exists in the form of clusters or aggregates at high concentration, the clusters or aggregates are fully reversible in nature.

Example 1-3 illustrate the excellent solubility and stability of exenatide in reservoirs of embodiments of the invention.

Example 4

The release rate profiles of exenatide through titania nanotube membranes were measured in a release rate study.

Four titanium reservoirs with a volume of 28 microliter were filled with a 5.7 mg of exenatide. A titania nanotube membrane was mounted on top of the reservoirs by means of a screw cap construction. The membrane comprised 5 windows, with an estimated total of about $60 \times 10^6$ nanotubes per window.

Figure 4:
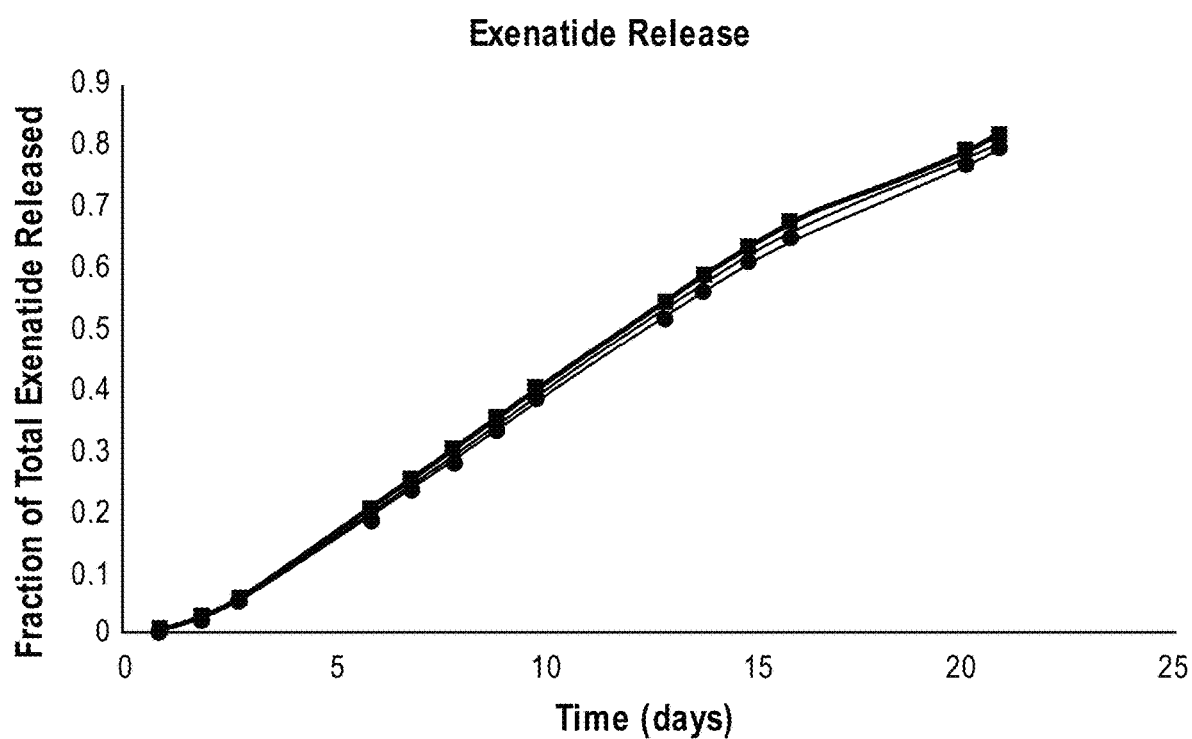
FIG. 4 illustrates zero order release of exenatide through a nanoporous membrane with pores larger than 5 times the Stokes' diameter of exenatide, using an initial solid exenatide formulation.

To accelerate hydration of the formulation, a vacuum was applied to the reservoirs through the nanotubes, and the evacuated reservoirs were exposed to phosphate buffered saline. The devices were then incubated at 37° C. for an extended period of time, with regular exchange of the release rate medium to measure released exenatide and to minimize degradation of exenatide in the release rate medium. The release rate profiles are illustrated in FIG. 4. Clearly, the release rate profiles of the exenatide are non-Fickian, and follow a good approximation of zero-order release until at least 80% of the total content is released at approximately 20 days.

The average pore sizes as determined by SEM analysis of the 4 membranes was 16.8, 17.6. 17.9 and 19.3 nanometer. At an estimated Stokes' diameter of exenatide of 2.6 nm, this corresponds to 6.5, 6.8, 6.9 and 7.4 times the Stokes' diameter of exenatide.

Example 5

6 devices with 28 microliter reservoirs were filled with a liquid exenatide formulation in a citrate buffer at pH 3.1. A nanotube membrane was mounted on top of each reservoir by means of a screw cap construction. The membrane comprised a single window with an estimated total of about $60 \times 10^6$ nanotubes.

Figure 5:
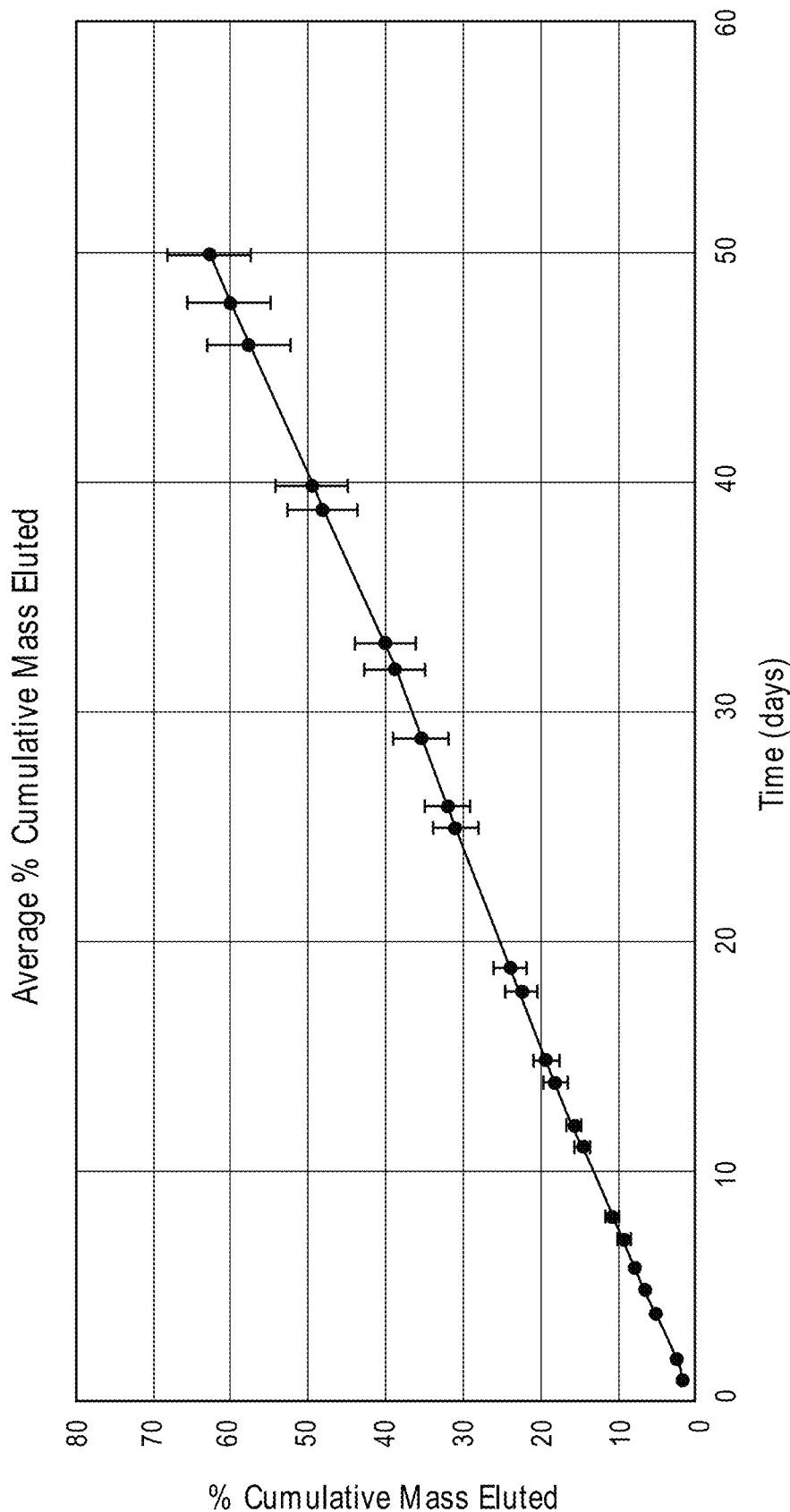
FIG. 5 illustrates zero order release of exenatide through a nanoporous membrane with pores larger than 5 times the Stokes' diameter of exenatide, using an initial liquid exenatide formulation.

The devices were then incubated at 37° C. for an extended period of time, with regular exchange of the release rate medium to measure released exenatide and to minimize degradation of exenatide in the release rate medium. The release rate profiles are illustrated in FIG. 5. Again, the release rate profiles of the exenatide are non-Fickian, and follow a good approximation of zero-order release until at least 70% of the total content is released (approximately 50 days).

Figure 6:
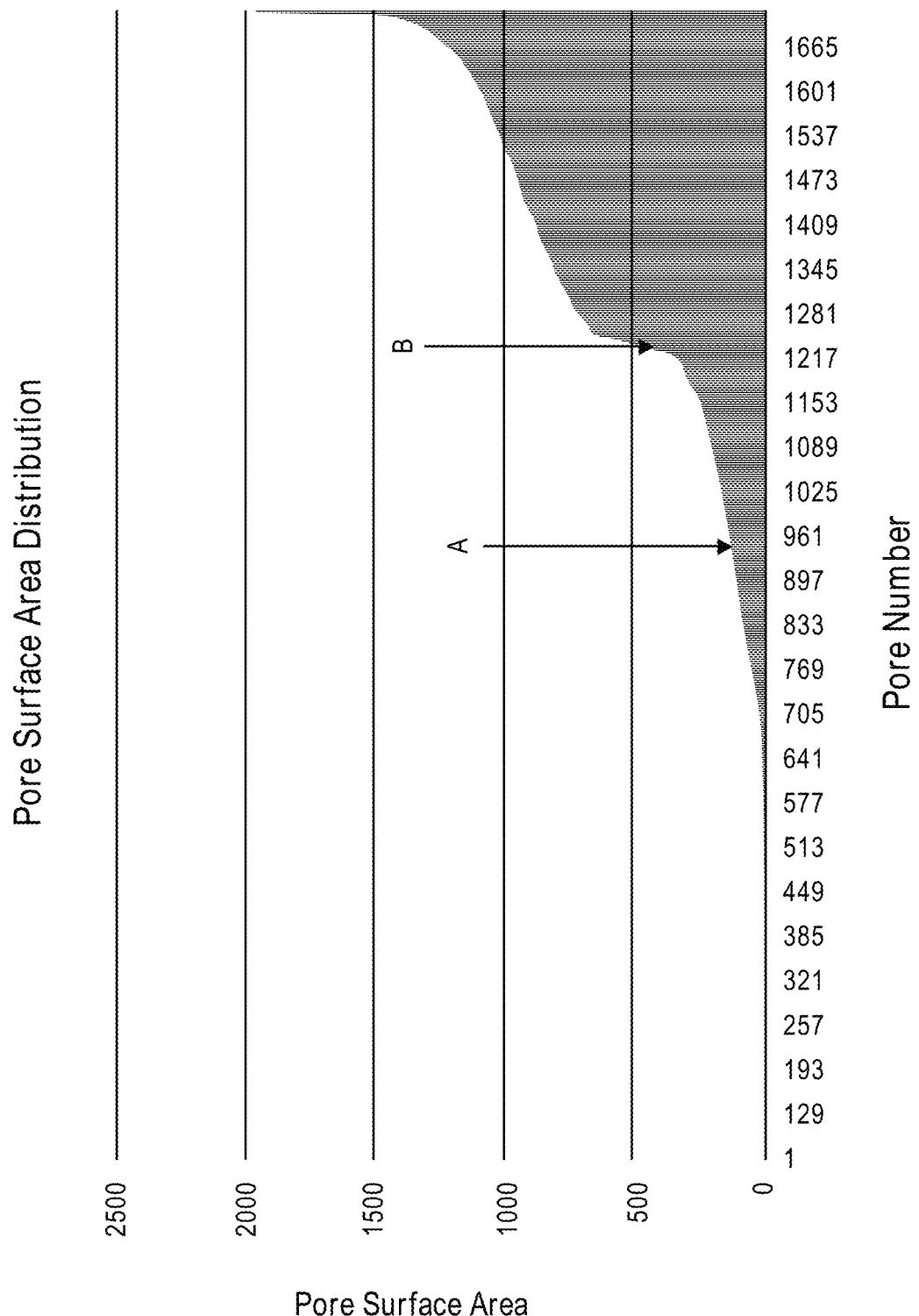
FIG. 6 illustrates one embodiment of pore size distribution, represented by cross-sectional surface area of a membrane from the same lot as used in FIG. 5.

FIG. 6 represents the pore size distribution in a sample of pores in a membrane from the same lot as the membranes in FIG. 5, characterized by SEM, and sorted by cross-sectional surface area. The X-axis represents the pore number, the Y-axis the cross-sectional surface area of the pores ($nm^2$). A representation by cross-sectional surface area is preferred over a representation by pore diameter, since diffusion scales directly with cross sectional surface area. The area under the curve in FIG. 6 therefore represents to total cross-sectional surface area available for diffusion.

As shown in FIG. 6, arrow A indicates the cut-off for pore sizes up to 5 times the hydrodynamic diameter of exenatide. All pores sizes to the left of A (about 1-920) are less than 5 times the hydrodynamic diameter of exenatide. Thus, 95.7% of the cross sectional area of aggregated pore size available for diffusion is contributed by pores larger than 5 times the hydrodynamic diameter of exenatide.

Arrow B indicates the cut-off for pore sizes up to 10 times the hydrodynamic diameter of exenatide. In this example, 83.5% of the aggregated cross sectional area available for diffusion is contributed by pores larger than 10 times the hydrodynamic diameter of exenatide. Unexpectedly, the largest pores in this sample have a diameter of almost 50 nm, or more than 19 times the hydrodynamic diameter of exenatide.

Whereas the embodiments and the examples in this disclosure describe zero-order release of a protein, the invention is not limited to protein delivery. Assuming validity of the supra-molecular aggregate hypothesis, other supra-molecular aggregates may be suitable for use in embodiments of the invention. Well-known examples of such aggregates include the complexation of iodine with poly-vinyl pyrrolidone, the complexation of heparin with large hydrophobic counterions like tri-dodecyl-methylammonium ions, and the complexation of many hydrophobic drugs with cyclodextrins.

Example 6

FIG. 7 shows a bi-model polydispersity of nanopore diameter sizes. There is a sharp peak to the far left having a pore distribution between about 2 nm to about 8 nm with a peak at about 4 nm. Another peak such as a bell curve is between 22 nm and about 39 nm with a maximum at 31 nm.

A monodispersity of nanopore diamters shows only 1 distribution of nanopore sizes. For example, there would be a sharp peak to the far left having a nanopore distribution between about 2 nm to about 8 nm with a peak maximum at about 4 nm only.

Alternatively, there is a bell curve between 22 nm and about 39 nm with a maximum at 31 nm only.

Embodiments of the present invention therefore offer the possibility to achieve zero-order release rate of therapeutic substances using nanopores with an inner diameter of more than 5 times a molecular diameter of the substances. The embodiments described above are strictly exemplary embodiments. They are included for the sole purpose of illustrating the invention with examples, and are not to be interpreted as limitations on the entire scope of the invention as described in this disclosure.

What is claimed is:

1. A method for non-Fickian release of a therapeutic agent from an implantable device, the method comprising:
providing the device, the device containing the therapeutic agent, wherein the therapeutic agent is exenatide, the device comprising:
a capsule suitable for implantation;
a reservoir encapsulated by the capsule, the reservoir suitable for containing a pharmaceutically acceptable formulation of the therapeutic agent;
at least one nanoporous membrane in fluid contact with the reservoir, wherein the nanoporous membrane comprises nanopores, wherein the nanopores have diameters of at least 6 times greater to about 19 times greater than the molecular diameter of the therapeutic agent, and
placing the device in an aqueous environment and allowing the non-Fickian release of the therapeutic agent.

2. The method of claim 1, wherein the molecular diameter is a Stokes' diameter of molecules of the therapeutic agent.

3. The method of claim 1, wherein the nanoporous membrane is a titania nanotube membrane.

4. The method of claim 1, wherein the pharmaceutically acceptable formulation comprises a solution of the therapeutic agent.

5. The method of claim 1, wherein the pharmaceutically acceptable formulation comprises a solid form of the therapeutic agent.

6. The method of claim 1, wherein the pharmaceutically acceptable formulation comprises the solid form of the therapeutic agent suspended in a liquid carrier.

7. The method of claim 1, wherein exenatide is present in an amount between about 50 micrograms to about 60 micrograms.

8. The method of claim 1, wherein the aqueous environment is a physiological environment.

9. The method of claim 8, wherein the physiological environment is a subcutaneous environment.

10. The method of claim 1, wherein the nanopores have a monodisperse distribution.

11. The method of claim 1, wherein the nanopores have a polydisperse distribution.

12. The method of claim 1, wherein the nanopores have a unimodal distribution.

* * * * *